US012708797B2

(12) United States Patent
Gao et al.

(10) Patent No.: US 12,708,797 B2
(45) Date of Patent: Aug. 18, 2026

(54) NEURAL NETWORK-BASED RADIATION TREATMENT PLANNING

(71) Applicant: Siemens Healthineers International AG, Steinhausen (CH)

(72) Inventors: Riqiang Gao, Plainsboro, NJ (US); Bin Lou, Princeton Junction, NJ (US); Ali Kamen, Skillman, NJ (US)

(73) Assignee: Siemens Healthineers International AG, Steinhausen (CH)

( * ) Notice: Subject to any disclaimer, the term of this patent is extended or adjusted under 35 U.S.C. 154(b) by 312 days.

(21) Appl. No.: 18/539,406

(22) Filed: Dec. 14, 2023

(65) Prior Publication Data

US 2025/0195919 A1 Jun. 19, 2025

(51) Int. Cl.
*A61N 5/10* (2006.01)
*A61B 6/03* (2006.01)
(Continued)

(52) U.S. Cl.
CPC ............ *A61N 5/1031* (2013.01); *A61B 6/032* (2013.01); *G16H 50/50* (2018.01); *G16H 50/70* (2018.01); *A61N 2005/1041* (2013.01)

(58) Field of Classification Search
CPC ....... A61B 6/032; A61B 6/469; A61B 6/5211; A61B 6/5258; A61B 6/466; A61B 34/10; A61B 5/7267; A61B 6/4085; A61B 6/5217; A61B 6/037; A61B 6/461; A61N 5/1031; A61N 2005/1041; A61N 5/1081; A61N 5/1071; A61N 5/1039; A61N 2005/1034; A61N 2005/1087; A61N 2005/1074; A61N 2005/1089; A61N 5/1036; A61N 5/1038; A61N 5/1045; A61N 5/1047; A61N 5/103; A61N 5/1048; A61N 5/1064; A61N 5/1084; G16H 20/40; G16H 50/70; G16H 50/50; G16H 50/20; G16H 30/40; G16H 40/63; G16H 10/60; G16H 40/67; G16H 30/20; G16H 40/20; G06N 3/047; G06N 3/006;
(Continued)

(56) References Cited

U.S. PATENT DOCUMENTS 10,475,537 B2 11/2019 Purdie
2019/0074079 A1 3/2019 Zankowski
(Continued)

OTHER PUBLICATIONS

Extended European Search Report from related European Patent Application No. 24219535.2 dated Apr. 9, 2025; 11 pages.
(Continued)

*Primary Examiner* — Irakli Kiknadze
(74) *Attorney, Agent, or Firm* — Fitch, Even, Tabin & Flannery LLP

(57) ABSTRACT

A neural network is trained using a training corpus having a plurality of information features, each of the information features including both a reference radiation treatment dose and at least one corresponding post-treatment patient datum. By one approach, the at least one corresponding post-treatment patient datum comprises patient imagery such as, but not limited to, one or more computed tomography images. That trained neural network facilitates radiation treatment planning by generating resultant treatment efficacy probability information and resultant treatment complications probability information.

17 Claims, 4 Drawing Sheets

(51) Int. Cl.
*G16H 50/50* (2018.01)
*G16H 50/70* (2018.01)

(58) Field of Classification Search
CPC .......... G06N 3/0464; G06N 3/08; G06N 3/09; G06N 3/092; G06N 3/045; G06N 7/01; G06N 3/084; G06N 3/094; G06N 3/096; G06N 3/0895; G06N 3/082; G06N 3/044; G06N 20/20; G06N 20/00; G06T 7/11; G06T 7/0012; G06T 2207/20084; G06T 2207/20081; G06T 2207/30096; G06T 11/008; G06T 7/64; G06T 1/20; G06T 7/30; G06T 2207/10088; G06T 2207/30004; G06T 2207/10081; G06T 2211/464; G06T 2211/441; G06T 5/60; G06T 5/50; G06T 5/70; G06T 2207/20221; G06T 2207/30196; G06T 2207/10016; G06V 10/7747; G06V 20/70; G06V 10/25; G06V 20/58; G06V 10/82; G06V 2201/07
USPC ...................................................... 378/62, 65
See application file for complete search history.

(56) References Cited

U.S. PATENT DOCUMENTS

2019/0332900 A1 10/2019 Sjolund
2022/0222873 A1 7/2022 Shreshtha
2023/0095485 A1* 3/2023 Czeizler ................ G16H 20/40 600/1
2023/0402151 A1* 12/2023 da Silva ............... A61N 5/1031

OTHER PUBLICATIONS

Barragán-Montero, A.M., et al.; Three-dimensional dose prediction for lung IMRT patients with deep neural networks: robust learning from heterogeneous beam configurations; Medical Physics, Aug. 2019; 46(8): 3679-3691. doi:10.1002/mp.13597.
Batmanghelich, Nematollah K., et al.; Probabilistic modeling of imaging, genetics and diagnosis; IEEE Transactions on Medical Imaging, Jul. 2016, 35(7): 1765-1779. doi:10.1109/TMI.2016.2527784.
Huynh, E., et al.; Artificial intelligence in radiation oncology; Nature Reviews Clinical Oncology, 2020, 17(12), 771-781. https://doi.org/10.1038/s41571-020-0417-8.
Kearney, V., et al.; DoseNet: a volumetric dose prediction algorithm using 3D fully convolutional neural networks. Physics in Medicine & Biology (2018).
Kohl, Simon, et al.; A probabilistic u-net for segmentation of ambiguous images; Advances in neural information processing systems; 32nd Conference on Neural Information Processing Systems (NeurIPS 2018), Montréal, Canada; https://arxiv.org/abs/1806.05034; 28 pages.
Kullback-Leibler divergence definition from Wikipedia https://en.wikipedia.org/wiki/Kullback%E2%80%93Leibler_divergence; 23 pages.
Lee, Hoyeon, et al.; Fluence-map generation for prostate intensity-modulated radiotherapy planning using a deep-neural-network. Scientific reports (2019) 9:15671; https://doi.org/10.1038/s41598-019-52262-x.
Li, Peng, et al.; Probabilistic Models for Inference About Identity; IEEE Transactions on Pattern Analysis and Machine Intelligence, Jan. 2012, 34(1): 144-157.
Liu, S., Zhang, J., Li, T., Yan, H., Liu, J.: Technical Note: A cascade 3D U-Net for dose prediction in radiotherapy. Medical physics 48(9), 5574-5582 (2021).
Nguyen, Dan, et al.; Incorporating human and learned domain knowledge into training deep neural networks: A differentiable dose volume histogram and adversarial inspired framework for generating Pareto optimal dose distributions in radiation therapy. Med Phys, Mar. 2020, 47(3): 837-849. doi:10.1002/mp.13955.
Nuraini, R., et al.; Tumor control probability (TCP) and normal tissue complication probability (NTCP) with consideration of cell biological effect; Journal of Physics: Conference Series, 1245 (2019) 012092. doi:10.1088/1742-6596/1245/1/012092.
Soomro, M.H., et al.; DeepDoseNet: A Deep Learning model for 3D Dose Prediction in Radiation Therapy; arXiv.org, Oct. 2021; https://doi.org/10.48550/arXiv.2111.00077.
Wang, Chunhao, et al.; Artificial intelligence in radiotherapy treatment planning: present and future; Technology in Cancer Research & Treatment, 2019, vol. 18, 1-11. DOI: 10.1177/1533033819873922.
Wang, Wentao, et al.; Fluence map prediction using deep learning models—direct plan generation for pancreas stereotactic body radiation therapy; Frontiers in Artificial Intelligence, Sep. 2020, vol. 3, Article 68. doi: 10.3389/frai.2020.00068.
Wang, Wentao, et al.; Deep Learning-Based Fluence Map Prediction for Pancreas Stereotactic Body Radiation Therapy With Simultaneous Integrated Boost; Advances in Radiation Oncology, (2021) 6, 100672. https://doi.org/10.1016/j.adro.2021.100672.
Xiong, Liang, et al.; Hierarchical probabilistic models for group anomaly detection; Proceedings of the 14th International Conference on Artificial Intelligence and Statistics (AISTATS); Journal of Machine Learning Research, Workshop and Conference Proceedings, 15:789-797, 2011.
Zaider M., et al.; Tumor control probability in radiation treatment; Medical Physics, Feb. 2011, 38(2): 574-583. doi: 10.1118/1.3521406.

* cited by examiner

NEURAL NETWORK-BASED RADIATION TREATMENT PLANNING

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often automatically generated through a so-called optimization process. As used herein, "optimization" will be understood to refer to improving a candidate treatment plan without necessarily ensuring that the optimized result is, in fact, the singular best solution. Such optimization often includes automatically adjusting one or more physical treatment parameters (often while observing one or more corresponding limits in these regards) and mathematically calculating a likely corresponding treatment result (such as a level of dosing) to identify a given set of treatment parameters that represent a good compromise between the desired therapeutic result and avoidance of undesired collateral effects.

Tumor control probability (TCP), which refers to the likelihood of tumor total destruction when administering radiation pursuant to a particular radiation treatment plan, and normal tissue complication probability (NTCP), which quantifies the probability of complications occurring in normal tissues surrounding the target area when exposed to radiation, can be used to measure the expected benefit of a given treatment plan and the expected damage on normal tissues. Striking an appropriate balance in those regards when formulating a radiation treatment plan, however, can be challenging. In practice, radiation treatment plans are often formulated by experienced oncologists and medical physicists who can differ in their views, and considerable inter-planner variability is often the result. The latter, in turn, can make it difficult to quantify the TCP and NTCP for a given radiation treatment plan.

BRIEF DESCRIPTION OF THE DRAWINGS

The above needs are at least partially met through provision of the neural network-based radiation treatment planning described in the following detailed description, particularly when studied in conjunction with the drawings, wherein.

Figure 1:
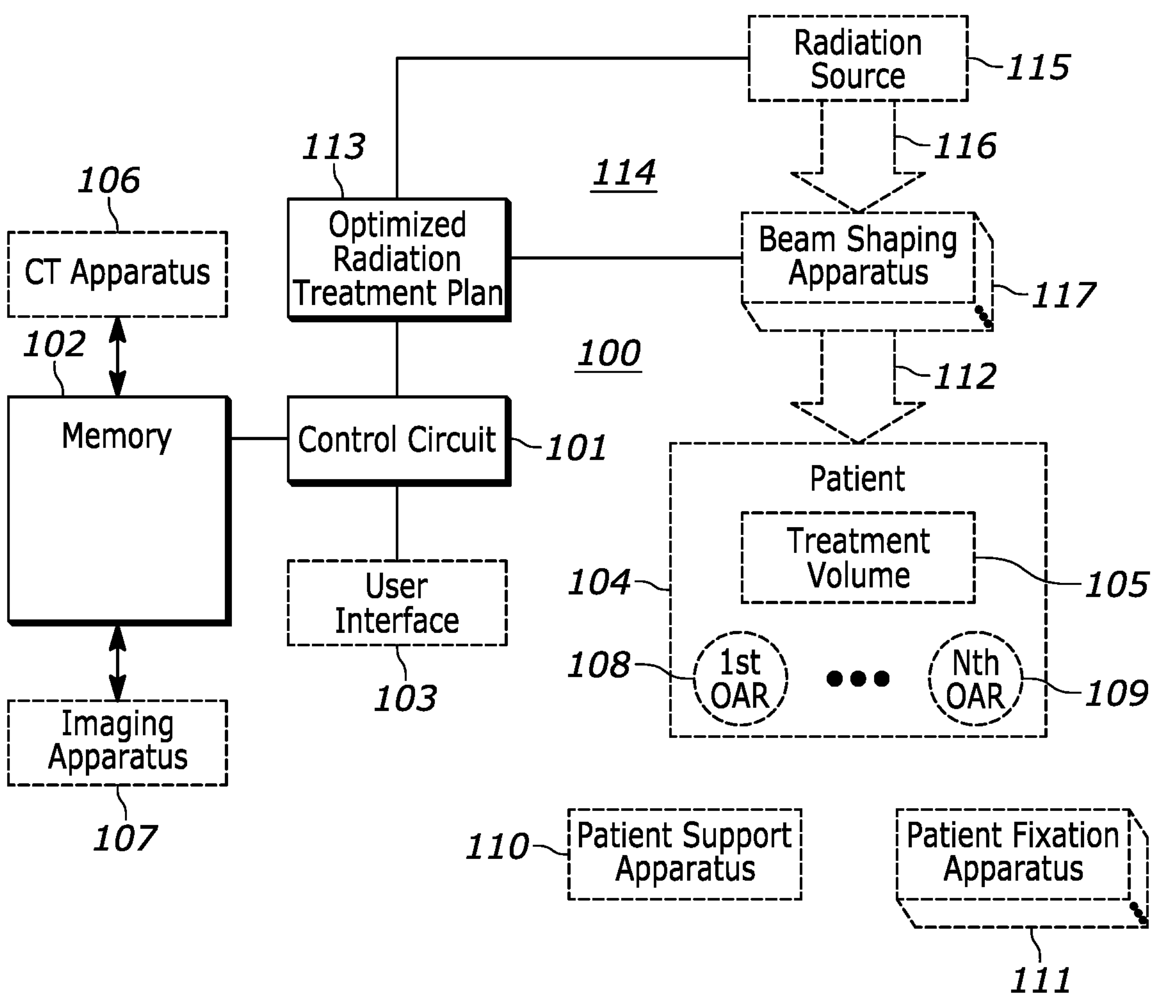
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, many of these various embodiments can provide for training a neural network that is configured to facilitate radiation treatment planning by generating resultant treatment efficacy probability information and resultant treatment complications probability information. These teachings can include accessing a training corpus having a plurality of information features, each of the information features including both a reference radiation treatment dose and at least one corresponding post-treatment patient datum. These teachings can then include training the neural network using that training corpus. By one approach, the at least one corresponding post-treatment patient datum comprises patient imagery such as, but not limited to, one or more computed tomography images.

By one approach, the neural network comprises a probabilistic model. In such a case, the probabilistic model may include a variational latent space in a radiation dose prediction pipeline.

By one approach, the neural network includes both an encoder and a decoder that are combined as a U-Net shape structure that receives multi-channel radiation treatment input for a particular patient and that outputs corresponding feature maps.

By one approach, the neural network can be configured to generate a prior latent space, wherein at least some positions in the prior latent space encode a corresponding radiation dose variant to provide a plurality of radiation dose variant codes. If desired, the neural network can be configured to output predicted radiation dose results from the plurality of radiation dose variant codes and feature maps.

By one approach, the aforementioned plurality of information features can include information representing a plurality of different patients and/or a plurality of different radiation treatment approaches.

So configured, these teachings will permit, for example, training a radiation treatment planning option space that allows users to benefit from a better quantifiable compromise between TCP and NTCP. These teachings also facilitate the use of a probabilistic model in the radiation treatment dose planning domain.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

It will be understood that a reference to a "control circuit" in the singular may reference a literal single discrete such circuit or may reference a plurality of discrete control circuits that can be viewed in the aggregate as a "control circuit." Accordingly, references to a "control circuit" will be understood to alternatively include either a single such device or a plurality of such devices in the absence of any language to the contrary.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. As one example, the control circuit 101 can be at least partially configured as a neural network in accord with the following description. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan (such as, for example, an optimized radiation treatment plan 113). This energy-based treatment plan typically comprises specified values for each of a variety of treatment-platform parameters during each of a plurality of sequential exposure fields. In this case the energy-based treatment plan is generated through an optimization process, examples of which are provided further herein.

By one approach the control circuit 101 can operably couple to an energy-based treatment platform 114 that is configured to deliver therapeutic energy 112 to a corresponding patient 104 having at least one treatment volume 105 and also one or more organs-at-risk (represented in FIG. 1 by a first through an Nth organ-at-risk 108 and 109) in accordance with the optimized energy-based treatment plan 113. These teachings are generally applicable for use with any of a wide variety of energy-based treatment platforms/apparatuses. In a typical application setting the energy-based treatment platform 114 will include an energy source such as a radiation source 115 of ionizing radiation 116.

By one approach this radiation source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the radiation source 115 along that arcuate pathway, and may accordingly control when the radiation source 115 starts moving, stops moving, accelerates, de-accelerates, and/or a velocity at which the radiation source 115 travels along the arcuate pathway.

As one illustrative example, the radiation source 115 can comprise, for example, a radio-frequency (RF) linear particle accelerator-based (linac-based) x-ray source. A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the radiation source 115, and one or more energy-shaping apparatuses (for example, beam-shaping apparatuses 117 such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
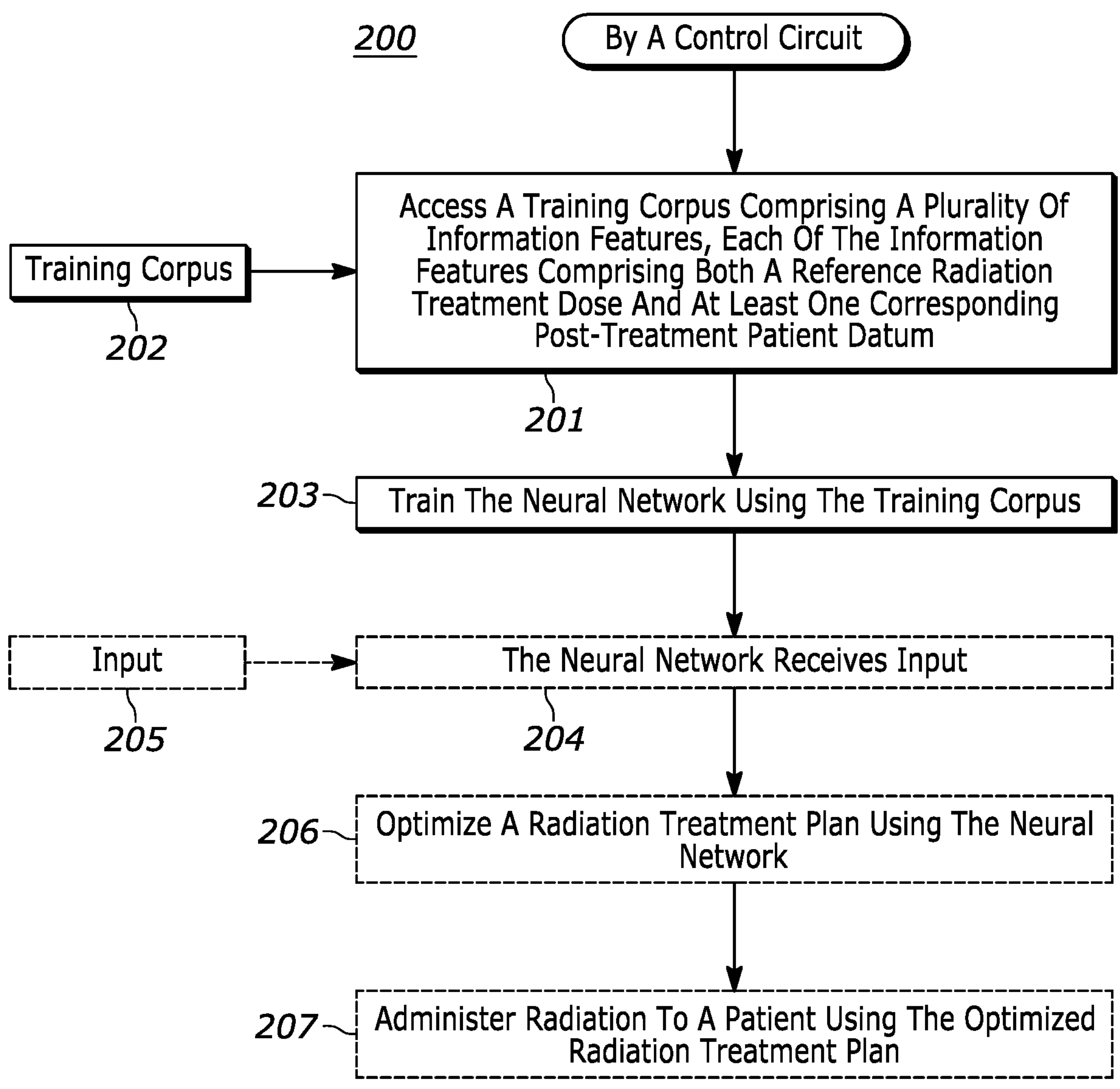
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 can serve to facilitate generating an optimized radiation treatment plan 113 to thereby facilitate treating a particular patient with therapeutic radiation using a particular radiation treatment platform per that optimized radiation treatment plan.

For the purposes of this example, it will be presumed that the control circuit 101 is configured, at least in part, as a neural network that facilitates radiation treatment planning by generating resultant treatment efficacy probability information and resultant treatment complications probability information. Without intending to suggest any particular limitations in these regards, the neural network can comprise a probabilistic model. A probabilistic neural network model is a type of artificial neural network that can be used for classification and pattern recognition tasks. The term "probabilistic" applies because such a network uses probability theory to make predictions and classify inputs.

By one approach, the foregoing probabilistic model can be configured to include a variational latent space in a radiation dose prediction pipeline. A variational latent space in a neural network prediction pipeline refers to modeling and representing complex data in a lower-dimensional space. In this context, the term "latent" refers to the hidden variables or factors that capture the underlying structure of the data. The variational aspect comes from the probabilistic nature of the model, which incorporates a probability distribution to model the latent space. In this example, the variational latent space can learn a low-dimensional representation of the input data that captures the essential features of the latter. The foregoing can include use of an encoder-decoder architecture, where the encoder network maps the input data to a latent space, and the decoder network reconstructs the input data from the latent representation. If desired, the such an encoder and a decoder that are combined as a U-Net shape structure that receives multi-channel radiation treatment input for a particular patient and outputs corresponding feature maps as described herein.

In lieu of the foregoing, or in combination therewith, the neural network can be configured, if desired, to generate a prior latent space where at least some positions in the prior latent space encode a corresponding radiation dose variant to provide a plurality of radiation dose variant codes. In such a case, the neural network can be configured to output predicted radiation dose results from the plurality of radiation dose variant codes and feature maps. These teachings will also accommodate, if desired, providing the user with an opportunity (for example, via the aforementioned user interface 103) to choose a particular plan based on their own preferences, guidelines, clinical best practices, or the like. In such a case, such a preference can be indicated in the latent space code (to indicate, for example, a preference for high TCP or high NTCP, where such a preference can be metricized in any of a variety of ways, including by referring to a ratio of a population such as, for example, specifying the top 50% TCP/NTCP of a given population as "high").

With reference to FIG. 2, at block 201, this process 200 provides for the aforementioned control circuit 101 accessing a training corpus 202 (as stored, for example, in the aforementioned memory 102). This training corpus 202 can include, but is not limited to, a plurality of information features. By one approach, each of these information features includes both a reference radiation treatment dose and at least one corresponding post-treatment patient datum. The aforementioned information features can include any of a variety of other content. Examples include (optionally or necessarily as desired), but are not limited to, patient-specific and/or radiation treatment platform-specific information such as computed tomography content, contouring/segmenting content, and radiation treatment platform geometry content.

By one approach, the plurality of information features includes information representing a plurality of different patients (including radiation treatment plan instructions and specifics). These different patients may all have been treated at a same radiation treatment facility/clinic or at least some of the patients may have been treated at differing facilities. By one approach, all of those patients were treated using the same radiation treatment approach. By another approach, at least some of the patients were treated using any of a plurality of different radiation treatment approaches.

The aforementioned post-treatment patient datum may include, by way of a non-limiting example, patient imagery such as, but not limited to, at least one patient computed tomography image. The latter may include computed tomography images for a patient as captured over a period of time, such as over a plurality of spaced-apart diagnostic and/or treatment sessions. These teachings will accommodate having some or all of the images be annotated in some regards (for example, to provide segmenting and/or contouring, or to highlight some feature or condition of interest).

At block 203, this process 200 then provides for training the neural network using the aforementioned training corpus 202. Training a neural network with a training corpus comprises a known area of prior art endeavor and generally comprises using a large dataset of (labeled and/or unlabeled) examples to teach the neural network to recognize patterns and make accurate predictions. Accordingly, for the sake of brevity, no further description is provided here regarding such training.

As noted above, the information features can include post-treatment patient datum that correspond to the aforementioned reference radiation treatment dose information. That post-treatment patient datum can include, for example, patient imagery such as one or more computed tomography images. So, as one example, a particular previously-administered radiation treatment plan that aimed to provide a radiation treatment dose of X Gy can be associated in the training corpus 202 with one or more post-treatment images that depict a post-treatment state of the targeted (and/or non-targeted) volume(s).

The result of the foregoing is a trained neural network that can output predicted radiation dose results and that can be beneficially leveraged in a radiation treatment planning option space.

With continued reference to FIG. 2, at optional block 204 the trained neural network receives input 205. That input 205 corresponds to a particular patient and/or radiation treatment platform and may comprise, for example, one, some, or all of computed tomography content (depicting, for example, relevant patient volumes), contouring/segmenting content (identifying particular patient volumes such as a target volume(s) and/or one or more organs-at-risk), and radiation treatment platform geometry content. As output, the trained neural network can yield a radiation dose (for one or more patient volumes) that can be then utilized when optimizing a particular radiation treatment plan for a particular patient.

And, as illustrated at optional block 206, these teachings will readily accommodate optimizing a radiation treatment plan using the neural network and, more particularly, the predicted output therefrom. At optional block 207, therapeutic radiation can then be administered to the corresponding patient using the so-optimized radiation treatment plan (using, for example, the above-described radiation treatment platform 114). As both radiation treatment plan optimization and the administration of a radiation treatment using an optimized plan are well understood areas of prior art endeavor, further explanation in those regards is not provided here.

Further examples that comport with these teachings will now be presented. It will be understood that the specific details of these examples are intended to serve an illustrative purpose and are not intended to suggest any particular limitations with respect to these teachings.

Figure 3:
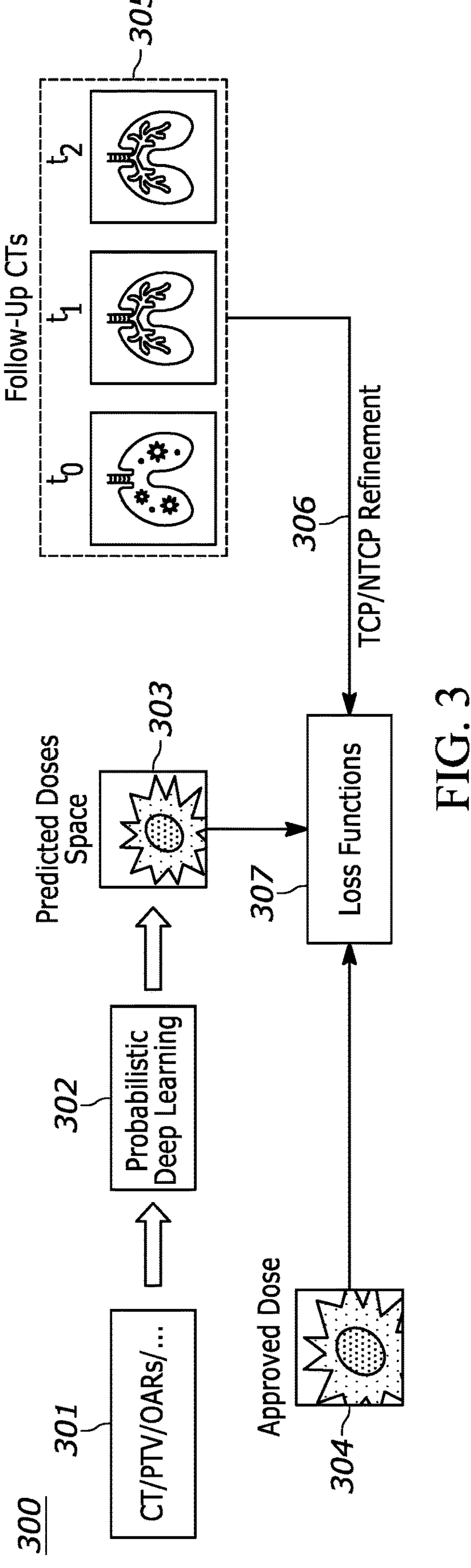
FIG. 3 comprises a schematic representation as configured in accordance with various embodiments of these teachings.

FIG. 3 presents an illustrative framework 300 for one approach in these regards. In this example, input 301 (including, for example, computed tomography images for a patient target volume(s) and/or one or more organs-at-risk) goes through a probabilistic deep learning model 302 to obtain a predicted dose space 303. An approved dose 304 can serve as a reference of predicted dose during training. Follow-up computed tomography images 305 provide image-based information 306 that can reflect the effectiveness of one or more previously-approved doses in terms of TCP and NTCP. (By one approach, the reference dose 304, and the follow-up image-based information 306 can be used during training, though not necessarily during inference activity.)

Figure 4:
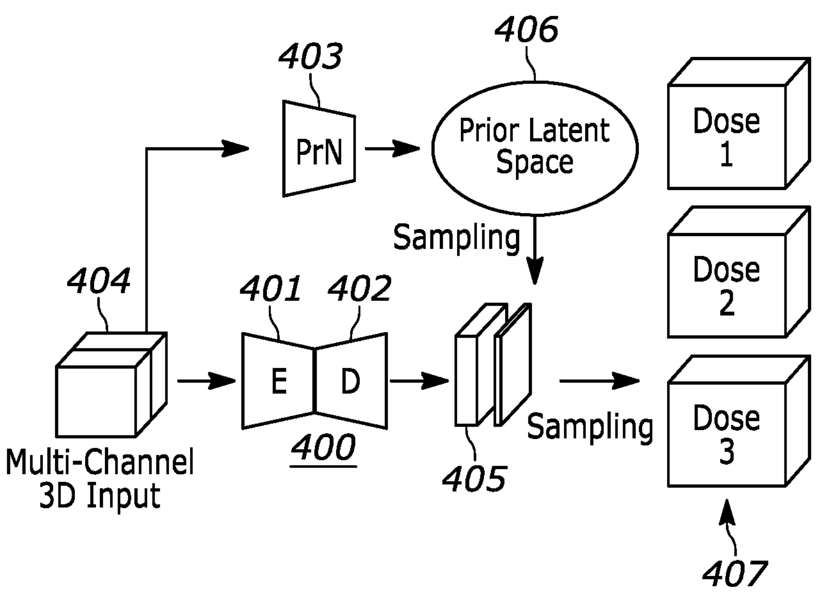
FIG. 4 comprises a schematic representation as configured in accordance with various embodiments of these teachings.
Figure 5:
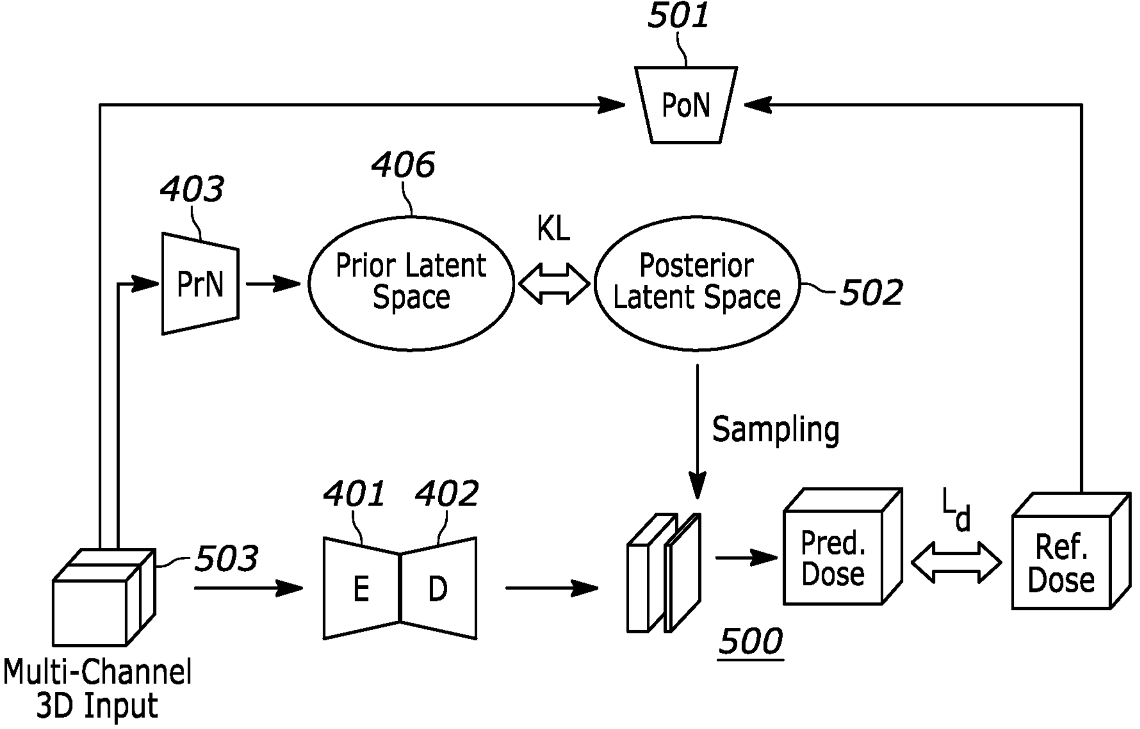
FIG. 5 comprises a schematic representation as configured in accordance with various embodiments of these teachings.

FIG. 4 presents an inference stage 400 and FIG. 5 presents a training stage 500 for a probabilistic model that can be employed in the foregoing examples to predict the dose space. These figures include an encoder 401 (E), a decoder 402 (D), a prior net 403 (PrN), and a posterior net 501 (PoN).

As regards the inference stage 400 shown in FIG. 4, the depicted approach includes a variational latent space in the dose prediction pipeline. In particular, the encoder 401 and the decoder 402 are combined as a U-Net shape-based convolutional neural network or transformer structure, which takes multi-channel three-dimensional input 404 and outputs three-dimensional feature maps 405. The prior net 403 builds a prior latent space 406, where (in this example) each position in this space 406 encodes a dose variant. The final predicted dose 407 results from the dose variant code and the three-dimensional feature maps 405 from the U-Net structure.

With reference to the training stage 500 shown in FIG. 5, the posterior net 501 generates another latent space 502 (referred to here as the posterior latent space and denoted as z in the following equations) using a three-dimensional (and multi-channel) input 503 (denoted as X in the following equations) and a reference dose map (denoted as Y in the following equations). There is a KL divergence loss that minimizes the different between the prior latent distribution 406 (denoted as P in the following equations) and the posterior latent distribution 502 (denoted by Q in the following equations). Accordingly, $$L_{KLD} = F_1(TCP(Y), NTCP(Y)) * D_{KL}(Q(z|Y, X) \| P(z|X)),$$

$$D_{KL}(Q \| P) = E_{z \sim Q}(\log Q - \log P)$$

where TCP(Y) and NTCP(Y) are the TCP/NTCP reflection from the planned reference dose map Y based on the follow-up computed tomography images, and $F_1(\cdot,\cdot)$ is an activation function (or, if desired, a neural network-based module) to transfer the impact from TCP(Y) and NTCP(Y) to the $L_{KLD}$ calculation.

Apart from $L_{KLD}$, there are other functions that can minimize the difference between the predicted dose $\hat{Y}$ and the reference dose Y. For example, $$L_d = F_2(TCP(Y), NTCP(Y)) * Dist(Y, \hat{Y})$$

where $Dist(Y, \hat{Y})$ measures the distance between Y and $\hat{Y}$ and $F_2(\cdot,\cdot)$ is an activation function (or, if desired, a neural network-based module) to transfer the impact from TCP(Y) and NTCP(Y) to the $L_d$ calculation. (By one approach, these teachings would accommodate having TCP(Y) and NTCP(Y) be vector valued quantities that can be assessed based on analyzing the follow-up computed tomography images and other clinical information from patients regarding the local control and degree of side effects.)

So configured, these teachings will support, for example, building an automatic dose planning space that can reflect and/or leverage toxicity factors from follow-up computed tomography images. These teachings can also provide a latent space that captures meaningful variants that, in turn, can allow users to choose plans by balancing the outcome against toxicity by considering different values during the aforementioned inference stage.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A method to train a neural network configured to facilitate radiation treatment planning by generating resultant treatment efficacy probability information and resultant treatment complications probability information, the method comprising:

accessing a training corpus comprising a plurality of information features, each of the information features comprising both a reference radiation treatment dose and at least one corresponding post-treatment patient datum;

training the neural network using the training corpus;

wherein the neural network comprises a probabilistic model that uses probability theory to make predictions and to classify inputs.

2. The method of claim 1 wherein the probabilistic model includes a variational latent space in a radiation dose prediction pipeline.

3. The method of claim 1 wherein the neural network includes an encoder and a decoder that are combined as a U-Net shape structure which receives multi-channel radiation treatment input for a particular patient and outputs corresponding feature maps.

4. The method of claim 1 wherein the neural network is configured to generate a prior latent space, wherein at least some positions in the prior latent space encode a corresponding radiation dose variant to provide a plurality of radiation dose variant codes.

5. The method of claim 4 wherein the neural network is configured to output predicted radiation dose results from the plurality of radiation dose variant codes and feature maps.

6. The method of claim 1 wherein the at least one corresponding post-treatment patient datum comprises patient imagery.

7. The method of claim 6 wherein the patient imagery comprises at least one patient computed tomography image.

8. The method of claim 1 wherein the plurality of information features includes information representing a plurality of different patients.

9. The method of claim 1 wherein the plurality of information features includes information representing a plurality of different radiation treatment approaches.

10. An apparatus comprising:

a control circuit configured as a neural network that facilitates radiation treatment planning by generating resultant treatment efficacy probability information and resultant treatment complications probability information, wherein the neural network was trained with a training corpus comprising a plurality of information features, each of the information features comprising both a reference radiation treatment dose and at least one corresponding post-treatment patient datum, and wherein the neural network comprises a probabilistic model that uses probability theory to make predictions and to classify inputs.

11. The apparatus of claim 10 wherein the probabilistic model includes a variational latent space in a radiation dose prediction pipeline.

12. The apparatus of claim 10 wherein the neural network includes an encoder and a decoder that are combined as a U-Net shape structure which receives multi-channel radiation treatment input for a particular patient and outputs corresponding feature maps.

13. The apparatus of claim 10 wherein the neural network is configured to generate a prior latent space, wherein at least some positions in the prior latent space encode a corresponding radiation dose variant to provide a plurality of radiation dose variant codes.

14. The apparatus of claim 13 wherein the neural network is configured to output predicted radiation dose results from the plurality of radiation dose variant codes and feature maps.

15. The apparatus of claim 10 wherein the neural network is configured to receive input comprising at least one of computed tomography content, contouring/segmenting content, and radiation treatment platform geometry content.

16. The apparatus of claim 15 wherein the neural network is configured to receive input comprising each of computed tomography content, contouring/segmenting content, and radiation treatment platform geometry content.

17. The apparatus of claim 10 wherein the plurality of information features includes information representing a plurality of different patients.

* * * * *